United States Patent [19]

Klun et al.

[11] 4,219,542
[45] Aug. 26, 1980

[54] SEX ATTRACTANT FOR TOBACCO MOTHS

[75] Inventors: Jerome A. Klun, Potomac; Jack R. Plimmer, Columbia; Barbara A. Bierl-Leonhardt, Potomac, all of Md.; Alton N. Sparks, Tifton, Ga.

[73] Assignee: The United States of America as represented by the Secretary of Agriculture, Washington, D.C.

[21] Appl. No.: 25,135

[22] Filed: Mar. 29, 1979

[51] Int. Cl.² ............................................. A01N 17/14
[52] U.S. Cl. ...................................................... 424/84
[58] Field of Search ........................................... 424/84

[56] References Cited

PUBLICATIONS

J. Chem. Ecol. 1, 203–214 (1975).
Life Sciences 14, 1555–1562 (1974).

Primary Examiner—Allen J. Robinson
Attorney, Agent, or Firm—M. Howard Silverstein; William E. Scott; David G. McConnell

[57] ABSTRACT

A combination of (Z)-11-hexadecenal, (Z)-9-tetradecenal, (Z)-9-hexadecenal, (Z)-7-hexadecenal, (Z)-11-hexadecen-1-ol, tetradecanal, and hexadecanal is an effective attractant for adult male tobacco budworm moths.

3 Claims, No Drawings

SEX ATTRACTANT FOR TOBACCO MOTHS

BACKGROUND OF THE INVENTION

1. Field of the Invention

This invention relates to insect attractants and more specifically to a highly effective attractant for the tobacco budworm.

2. Description of Prior Art

Attractants for some insect species are known in the art. For example, hexalure, cis-7-hexadecen-1-ol acetate is an effective attractant for adult male pink bollworm moths, *Pectinophora gossypiella* (Saunders). However, propylure, the sex pheromone isolated from virgin pink bollworm moths failed to attract the male pink bollworm in the field (Science 152, 1516-17, 1966). In fact, (Z)-11-hexadecenal, one of the components of the attractant of this invention and also one of the components of an attractant for corn earworm moths was found to inhibit the catch of male corn earworm adults by virgin females of the same species (J. Econ. Entomology 68, 603-4, 1975). As little as 5 mg of (Z)-11-hexadecenal resulted in 50% inhibition of male catch by four virgin females while 50 mg inhibited the catch in excess of 99%.

BRIEF SUMMARY OF THE INVENTION

An object of this invention is to provide an attractant for adult male tobacco budworm moths.

A further object is to provide a method of attracting and trapping adult male tobacco budworm moths.

A still further object is to provide a means of interfering with mating communication of tobacco budworm moths and thereby suppress the population of the moths.

Still another object is to provide a means to detect infestations of the tobacco budworm, to delineate infested areas, and to estimate tobacco budworm population densities.

In general, according to this invention, a novel combination of (Z)-11-hexadecenal, (Z)-9-hexadecenal, (Z)-7-hexadecenal, (Z)$_{14}$-9-tetradecenal, (Z)-11-hexadecen-1-ol, hexadecanal, and tetradecanal is found to be an effective attractant for adult male tobacco budworm moths. The new attractant can be used to bait a trap or it can be used to suppress tobacco budworm populations by permeating the atmosphere in an infected area. The latter interferes with mating communication causing substantial disruption of mating and consequent reduction in insect population.

DESCRIPTION OF THE INVENTION

Many major insect pests infest corn, cotton, tobacco and other crops and their larvae cause considerable economic loss, to the extent that cultivation of these crops may not be possible in certain areas. Chemical pesticide sprays have been used to control the insects responsible for crop damage for many years, but the intensive use of conventional chemicals may ultimately present hazards to man and the environment and it has frequently resulted in the survival of insecticide-resistant insect populations that can no longer be treated effectively. Therefore, insecticidal chemicals should be used only when the population of pest species rises to levels that could result in substantial economic loss. Methods of pest control that offer an alternative to the use of conventional chemicals are needed.

Females of many lepidopteran species attract males by emitting a sex attractant pheromone. If the active component(s) of the pheromone can be isolated and indentified, this material can be used as a lure in an insect trap to attract and catch male moths. The pheromone is slowly vaporized from a suitable formulation and the male moth enters and trap where it is held or killed. If such traps are situated in the area in which an infestation of moths may occur, the presence of moths can then be detected. Thus, the application of pesticides can be delayed until the number of insects in the traps reaches a predetermined level when crop damage might occur. Pheromones may also be used to attract male insects to traps or alternative locations in sufficient numbers to interrupt the reproductive cycle and reduce the numbers of pests in subsequent generations.

A further application of insect sex pheromones or attractants is their use to suppress insect populations in infested areas by interfering with mating communication. If the air throughout the area is permeated with the compounds, substantial mating disruption may result, with a consequent reduction in insect population.

The tobacco budworm *Heliothis virescens*, is a major pest of cotton and tobacco in the United States. The sex pheromone contains a blend of chemicals that serves as a powerful attractant for male moths. Thus, these chemicals may be utilized for monitoring insect populations or they may have value in air permeation techniques to reduce population. The compounds (Z)-11-hexadecenal and (Z)-9-tetradecenal were isolated previously as components of the sex pheromone (Roelofs et al., 1974, Tumlinson et al., 1975). We identified a mixture of seven compounds in the pheromone system, namely, (Z)-11-hexadecenal, (Z)-7-hexadecenal, (Z)-9-hexadecenal, (Z)-11-hexadecen-1-ol, hexadecanal, tetradecanal and (Z)-9-tetradecenal in the ratios 76:2:3:6:7:15:45.

Various materials and methods are employed to extract, isolate, and identify the active compounds in the pheromone of the female tobacco budworm moth and to test the behavioral responses of the male moth to the synthetic compounds. The methods of synthesis of the compounds have been described in the chemical literature, but we found that they must be rigorously purified and protected from oxidative degradation as described later under Purification of Synthetic Compounds as impurities render them ineffective.

MATERIALS AND METHODS

Pupae were obtained from cultures of *H. virescens* at USDA Laboratories in Fargo, ND, Stoneville, MS or Brownsville, TX and were separated by sex. The females were isolated individually under constant light at 22°-26° to await emergence. Adult females were held 1 to 4 days after emergence. The ovipositor was forcibly everted by exerting pressure on the abdomen of the insect. The ovipositor was carefully excised with fine dissecting scissors through the middle of the tergum of the 8th abdominal segment which is located anterior to the ovipore. The newly cut surface of the ovipositor tip was placed briefly on a filter paper to absorb hemolymph, and the tip was then placed in a specially designed ampoule or micro vial containing heptane (3 μl) and an internal standard (4 ng.) (Z)-11-tridecenyl acetate). A description of the ampoule is found in J. Chem. Ecology 3, 447-459, 1977, and is considered incorporated into this specification.

The heptane extract (3 μl) was analyzed on a gas chromatograph equipped with a microprocessor-controlled splitless injector system and a flame ionization detector (Hewlett-Packard Model 5840A). The carrier gas used was helium, flow rate 2 ml./min at 120° C. column temperature, injector temperature 225° C. The injector was purged 1.1 minutes after injector. The column was temperature-programmed; 120° C. at injection held for 2 minutes, then heated at 30°/min to 180° C. (polyethylene glycol-20M-nitroterephthalic, Supelco SP1000 column) or to 200° C. (methyl silicone fluid, Supelco SP2100 column). The columns used were glass open-tubular capillary (60 m×0.2 mm id) coated with either SP1000 or SP2100.

Mass spectra were obtained with a combined gas chromatograph-mass spectrometer (Finnigan Model 4000), equipped with a data system Finnigan 6110 Data System). The gas chromatograph of the mass spectrometer was equipped with a SP2100 wall-coated open tubular glass capillary column (30 m×0.25 mm I.D.) that could be operated in the splitless mode. The total volume of the column effluent was admitted to the mass spectrometer source.

Behavioral response assays were conducted in cylindrical screened cages (13.5 cm×7 cm O.D.). Air from an outside source was pumped through a 10.3 cm tube and delivered at 1.5–1.8 m/sec flow rate. Males were obtained from laboratory cultures and held in a 16:8 LD (Light to dark) regime at 26° C. for 3 to 5 days after emergence from pupae. Sets of 8 to 10 adult males were held at 20° C. in cages for each bioassay, which consisted of a 30 sec. exposure to a chemical stimulus on the tip of a disposable glass pipet held 4 cm upwind of the cage. Airflow downwind was exhausted through the vent of a laboratory fume hood. Each test was scored by the number of males that responded to the stimulus with wind vibration, extension of scent brushes and genitalia, and clasper responses within the 30 seconds exposure to the stimulus. Selected sets of olefinic aldehydes were tested in combination with (Z)-11-hexadecenol, tetradecanal, and hexadecanal.

Field tests were conducted in a tobacco field near Tifton, Georgia. Traps were constructed of 2 plastic plates 25 cm diameter and 2.5 cm apart, separated by a centrally positioned cylinder formed of hardware cloth. The upper surface of the bottom plate was coated with a commercially available substance for holding the trapped insects. One of the substances which we used was Stickem Special, a combination of 40 parts polymerized 1-butene, 35 parts polymerized 2-methyl propene, and 14 parts polymerized butane, in paraffin wax. Any other available product to which the insects would stick and be held in a trap is suitable for the purposes of this invention. The traps were deployed 1.5 m above the ground on metal stakes and 20 m apart at the perimeter of a cotton field and within the *H. virescens* patent alleyways of a tobacco field. The field test was run over 6 consecutive nights using randomized complete-block design with 6 treatments and 7 replicates.

Test chemicals dissolved in 10 μl heptane containing 2,6-di-tert-butyl-4-methylphenol as antioxidant were evaporated from cotton dental rolls 1.5 cm in length. The cottom rolls were placed on the sticky surface near the center of the lower plate of the tray described above. Each roll was removed in the morning and replaced with new freshly treated rolls about one hour before sunset each day.

Check traps were baited with three 2-to 7-day old females contained in a cylindrical cage that fitted into the hardware cloth cylinder used as a trap spacer. The moths were obtained from the USDA Tifton, GA., Laboratory culture as pupae and were allowed to emerge under ambient conditions.

Isolation and Identification of the Active Compounds

The ovipositor wash (3 μl, one female equivalent) of the tobacco budworm was injected into the gas chromatograph operated in the splitless injection mode. Seven compounds were identified by their retention times, which were identical with those of authentic compounds on both SP2100 and SP1000 columns. Their identities were comfirmed by combined gas chromatograph-mass spectrometry of the wash before and after epoxidation with m-chloroperbenzoic acid. As noted above, two compounds, (Z)-11-hexadecenal and (Z)-9-tetradecenal, have previously been identified in extracts of *Heliothis virescens*. Four of the components, (Z)-7-hexadecanal, (Z)-9-hexadecenal, (Z)-11-hexadecenal and hexadecanal, were identical to those identified by us in H. zea ovipositor washes. Three additional compounds present in the ovipositor wash of *H. virescens* were not found in *H. zea*. The retention times ($T_r$) of these components on the 60 m×0.5 m i.d. SP2100 and SP1000 columns were the same as those of authentic (Z)-9-tetradecenal, tetradecanal, and (Z)-11-hexadecen-1-ol, respectively.

Mass spectra were obtained on the above three compounds. The mass spectrum of the compound identified as (Z)-9-tetradecenal was consistent with a $C_{14}$-monounsaturated aldehyde structure. It had a fragment ion $M^+$-18 at m/e 192 and a base peak at m/e 67, which indicates that it is (Z)-9-tetradecenal. The mass spectrum of the compound identified as tetradecanal had $M^+$-18 at m/e 194, $M^+$-44 at m/e 168, and a base peak at m/e 82. The molecular ion (m/e 212) was noted detected but the fragmentation pattern at lower masses corresponded to that of authentic tetradecanal. The mass spectrum of the compound identified as (Z)-11-hexadecen-1-ol was identical with that of a $C_{16}$ monounsaturated primary alcohol. It had $M^+$-18 at m/e 222 and a bare peak at m/e 55. Since the fragmentation patterns of the epoxides often contain intense peaks that reveal the location of the epoxide function, some of the wash was converted to the epoxides by reaction with m-chloroperbenzoic acid. The epoxidized ovipositor wash contained a component that had mass spectrum and gas chromatographic open tubular capillary column retention time identical to that of authentic cis-11,12-epoxy-hexadecan-1-ol. These data show that the compound corresponds to (Z)-11-hexadecen-1-ol.

Testing Male Behavioral Responses

Laboratory behavioral assays.

Combinations of synthetic materials purified as described later were tested in the laboratory as described above under Materials and Methods. Each set of 10 caged males was exposed to only one stimulus for 30 seconds and then discarded. The number of males that responded by wing vibrations, extension of genitalia and clasper response was recorded. Table 1 shows the percentage male response to combinations of olefinic aldehydes.

Further laboratory bioassay results are shown in Table 2 which shows that the addition of (Z)-11-hexadecen-1-ol or saturated aldehydes had no significant effect and that the binay mixture of (Z)-11-hexadecenal and (Z)-9-tetradecenal alone elicited maximum male response. In the laboratory bioassay the activity of the binary mixture was not significantly increased when other pheromone components were added.

Field Tests.

Field tests were conducted as described under Materials and Methods. Although combinations of (Z)-11-hexadecenal and (Z)-9-tetradecenal elicited maximum male response in the laboratory bioassay, this combination did not adequately elicit male response in field tests. The field test data in Table 3 show that this binary mixture was about one-fifth as effective in attracting males as the full complement of compounds identified in *H. virescens* females. A mixture of the 4 olefinic aldehydes was not significantly different from the binary mixture, but the combination of (Z)-11-hexadecen-1-ol with the 4 olefinic aldehydes was significantly more attractive to males then the 4 olefinic aldehydes alone. The mixture containing the 4 olefinic aldehydes plus (Z)-11-hexadecen-1-ol, hexadecanal and tetradecanal was superior to any other treatment (including virgin females) as a male attractant.

Purification of Synthetic Compounds

Compounds present in the ovipositor wash can be purchased commercially or synthesized by methods described in the chemical literature. Before use they were purified to greater than 99.9% purity as indicated by glc analysis on the SP1000 chromatographic column.

Final purification was achieved by high pressure liquid chromatography on silica treated with silver nitrate (J. Chromat. Sci. 15, 10–13, 1977). The effluent from the high pressure liquid chromatograph, containing the desired compound, was collected in a reservoir containing 2,6-di-tert-butyl-4-methylphenol (antioxidant). Use of antioxidants in combination with the aldehydic compounds is required for protection of unsaturated aldehydes from oxidation and to retain biological activity.

Table 1

Male *Heliothis virescens* sex stimulation responses in laboratory assays to combinations of olefinic aldehydes identified from the female ovipositor.

| ng Stimulus[1] | x̄ Percentage Male response[2] |
|---|---|
| 115.5 Z-11 | 29.98 e[3] |
| 115.5 Z-11 + 1.3 Z-7 | 37.06 de |
| 115.5 Z-11 + 2.25 Z-9 | 47.56 cde |
| 115.5 Z-11 + 7.95 Z$_{14}$-9 | 78.82 ab |
| 115.5 Z-11 + 1.3 Z-7 + 2.25 Z-9 | 55.57 bcd |
| 115.5 Z-11 + 1.3 Z-7 + 2.25 Z-9 + 7.95 Z$_{14}$-9 | 82.67 a |
| 115.5 Z-11 + 1.3 Z-7 + 7.95 Z$_{14}$-9 | 69.21 abc |
| 115.5 Z-11 + 2.25 Z-9 + 7.95 Z$_{14}$-9 | 86.21 a |

[1]Z-11 = (Z)-11-hexadecenal, Z-7 = (Z)-7-hexadecenal Z-9 = (Z)-9-hexadecenal, Z$_{14}$-9 = (Z)-9-tetradecenal
[2]Bioassays were conducted as described under Materials and Methods. The tests were conducted in a randomized complete-block design with ten replicates. In each replicate a separate set of 10 caged males was exposed to each treatment. Thus, ca. 100 males (in sets of ten) were exposed to each stimulus. The percentage male response indicates the average number of males that responded to each stimulus during a 30 second exposure. Each set of 10 males was exposed to only one stimulus and then discarded.
[3]Means followed by the same letter are not significantly different from each other at $P = 0.05$ according to Duncan's new multiple range test.

Table 2

Male *Heliothis virescens* sex stimulation responses in laboratory assays to combinations of compounds identified from the female ovipositor

| ng Stimulus[1] | x̄ Percentage Male Response[2] |
|---|---|
| 57.75 Z-11 + 3.45 Z$_{14}$-9 | 89.4 a |
| 57.75 Z-11 + 3.45 Z$_{14}$-9 + 2.25 Z-9 + 1.3 Z-7 | 78.5 a |
| 57.75 Z-11 + 3.45 Z$_{14}$-9 + 2.25 Z-9 + 1.3 Z-7 + 4.5 Z-11-OH | 78.5 a |
| 57.75 Z-11 + 3.45 Z$_{14}$-9 + 2.25 Z-9 + 1.3 Z-7 + 4.5 Z-11-OH + 1.25 C$_{14}$ + 5.5 C$_{16}$ | 82.5 a |

[1]Z-11 = (Z)-11-hexadecenal, Z$_{14}$-9 = (Z)-9-tetradecenal, Z-9 = (Z)-9-hexadecenal, Z-7-hexadecenal, Z-11-OH = (Z)-11-hexadecen-1-ol, C$_{14}$ = tetradecanal, C$_{16}$ = hexadecanal
[2]Means followed by the same letter are not significantly different from each other at $P = 0.05$.

Table 3

Male *Heliothis virescens* sex stimulation responses in field bioassay to combinations of compounds identified from the female ovipositor.

| μg Stimulus[1] | x̄ male/trap[2] |
|---|---|
| 115.5 Z-11 | 0.1 c |
| 115,.5 Z-11 + 6.9 Z$_{14}$-9 | 2.4 c |
| 115.5 Z-11 + 6.9 Z$_{14}$-9 + 4.5 Z-9 + 2.6 Z-7 + Z-11-OH | 3.0 c |
| 115,5 Z-11 + 6.9 Z$_{14}$-9 + 4.5 Z-9 + 2.6 Z-7 + 9 Z-11-OH | 7.9 b |
| 115.5 Z-11 + 6.9 Z$_{14}$- 9 + 4.5 Z-9 + 2.6 Z-7 + 0 Z-11-OH + 2.25 C$_{14}$ + 11 C$_{16}$ | 14.5 a |
| 4 virgin females | 4.8 bc |

[1]Z-11 = (Z0-11-hexadecenal, Z-7 = (Z)-7-hexadecenal, Z-9 = (Z)-9-hexadecenal, Z$_{14}$-9 = (Z)-9-tetradecenal, Z-11-OH = (Z)-11-hexadecen-1-ol, C$_{14}$ = tetradecanal, C$_{16}$ =0 hexadecanal.
[2]Means followed by the same letter are not significantly different from ech other at $P = 0.05$.

We claim:

1. An attractant for the adult male tobacco budworm comprising an effective attractant amount of an effective combination of (Z)-11-hexadecenal, (Z)-9-tetradecenal, (Z)-9-hexadecenal (Z)-7-hexadecenal, (Z)-11-hexdecen-1-ol, tetradecanal, and hexadecanal, said components being at least 99.0% pure and combined at ratios of about 11.5:6.9; 4.5; 2.6; 9.0; 2.25; and 11.0, on a weight basis, and an effective antioxidant amount of 2,6-di-tert-butyl-4-methyl phenol.

2. A method of attracting adult male tobacco budworm moths comprising baiting a trap with an effective attractant amount of an effective attractant combination of (Z)-11-hexadecenal, (Z)-9-tetradecenal, (Z)-9-hexadecenal, (Z)-7-hexadecenal, (Z)-11-hexadecen-1-ol, tetradecanal, and hexadecanal, said components being at least 99.0% pure and combined at ratios of about 115.5; 6.9; 4.5; 2.6; 9.0; 2.25; and 11.0, on a weight basis, and an effective antioxidant amount of 2,6-di-tert-butyl-4-methyl phenol.

3. A method of suppressing the population of tobacco budworms in infected areas comprising permeating the atmosphere in said area with an effective attractant combination of (Z)-11-hexadecenal, (Z)-9-tetradecenal, (Z)-9-hexadecenal, (Z)-7-hexadecenal, (Z)-11-hexadecen-1-ol, tetradecanal, and hexadecanal, said components being at least 99.0% pure and combined at ratios of about 115.5; 6.9; 4.5; 2.6; 9.0; 2.25; and 11.0, on a weight basis, and an effective antioxidant amount of 2,6-di-tert-butyl-4-methyl phenol.

* * * * *